(12) United States Patent
Schowalter et al.

(10) Patent No.: US 11,530,141 B2
(45) Date of Patent: Dec. 20, 2022

(54) SYSTEMS AND METHODS FOR FLUID DISINFECTION WITH ULTRAVIOLET LIGHT

(71) Applicant: Crystal IS, Inc., Green Island, NY (US)

(72) Inventors: Leo J. Schowalter, Latham, NY (US); Amy C. Wilson Miller, Ballston Lake, NY (US)

(73) Assignee: Crystal IS, Inc., Green Island, NY (US)

( * ) Notice: Subject to any disclaimer, the term of this patent is extended or adjusted under 35 U.S.C. 154(b) by 55 days.

(21) Appl. No.: 16/672,450

(22) Filed: Nov. 2, 2019

(65) Prior Publication Data

US 2020/0140292 A1 May 7, 2020

Related U.S. Application Data

(60) Provisional application No. 62/755,041, filed on Nov. 2, 2018.

(51) Int. Cl.
*C02F 1/32* (2006.01)
*A61L 2/26* (2006.01)
*A61L 2/10* (2006.01)

(52) U.S. Cl.
CPC ............... *C02F 1/325* (2013.01); *A61L 2/10* (2013.01); *A61L 2/26* (2013.01); *A61L 2202/11* (2013.01);
(Continued)

(58) Field of Classification Search
CPC ...... C02F 1/32; C02F 1/72; C02F 1/78; C02F 1/48; C02F 1/46; A61L 2/10; B01D 32/34; B01D 61/10; B01D 61/08
See application file for complete search history.

(56) References Cited

U.S. PATENT DOCUMENTS

| 4,111,538 A | 9/1978 | Sheridon |
| 6,365,920 B1 | 4/2002 | Abramov et al. |

(Continued)

FOREIGN PATENT DOCUMENTS

| CN | 212894017 U | * | 4/2021 | ............ C02F 1/32 |
| WO | WO-2014187524 A1 | * | 11/2014 | ............ C02F 1/325 |
| WO | 2018190667 A2 | | 10/2018 | |

OTHER PUBLICATIONS

International Search Report and Written Opinion for Application No. PCT/US19/59568, dated Jan. 24, 2020 (19 pages).

(Continued)

*Primary Examiner* — Cameron J Allen
(74) *Attorney, Agent, or Firm* — Nutter McClennen & Fish LLP

(57) ABSTRACT

A fluid treatment system includes a reactor chamber fluidly coupled with a fluid inlet and a fluid outlet. The reactor chamber is defined by one or more chamber walls. The system includes a UV LED, and a light pipe. The light pipe extends into the reactor chamber through at least one of the chamber walls. The light pipe has a proximal end disposed outside of the reactor chamber. The proximal end is coupled with the UV LED to transmit UV light into the reactor chamber through the light pipe. To that end, the light pipe also has a distal end, opposite the proximal end, that is disposed within an interior volume of the reactor chamber. The light pipe includes a central section disposed between the proximal end and the distal end. The central section is configured to transmit the UV light from UV LED to the distal end.

22 Claims, 10 Drawing Sheets

(52) U.S. Cl.
CPC . *A61L 2202/122* (2013.01); *C02F 2201/3222* (2013.01); *C02F 2201/3225* (2013.01); *C02F 2201/3227* (2013.01); *C02F 2201/3228* (2013.01); *C02F 2303/04* (2013.01)

(56) References Cited

U.S. PATENT DOCUMENTS

| | | |
|---|---|---|
| 6,961,190 B1 | 11/2005 | Tamaoki et al. |
| 7,638,346 B2 * | 12/2009 | Schowalter ....... H01L 21/02389 117/104 |
| 7,832,885 B2 | 11/2010 | Hsiao et al. |
| 8,962,359 B2 | 2/2015 | Schowalter et al. |
| 10,074,784 B2 | 9/2018 | Schowalter et al. |
| 2002/0126468 A1 | 9/2002 | Umemoto et al. |
| 2007/0091633 A1 | 4/2007 | Harrity et al. |
| 2008/0023719 A1 | 1/2008 | Camras et al. |
| 2009/0072263 A1 | 3/2009 | Paolini et al. |
| 2010/0025713 A1 | 2/2010 | Tao et al. |
| 2011/0136394 A1 | 6/2011 | Mostoller et al. |
| 2012/0069564 A1 | 3/2012 | Andrews et al. |
| 2012/0228236 A1 | 9/2012 | Hawkins, II et al. |
| 2013/0323128 A1 | 12/2013 | Owen et al. |
| 2015/0053624 A1 * | 2/2015 | Maiden ................... C02F 1/325 210/748.11 |
| 2015/0129776 A1 * | 5/2015 | Boodaghians .......... C02F 1/325 250/432 R |
| 2019/0035992 A1 | 1/2019 | Schowalter et al. |

OTHER PUBLICATIONS

Extended European Search Report for Application No. 19878215.3 dated Jun. 15, 2022, 9 pages.

* cited by examiner

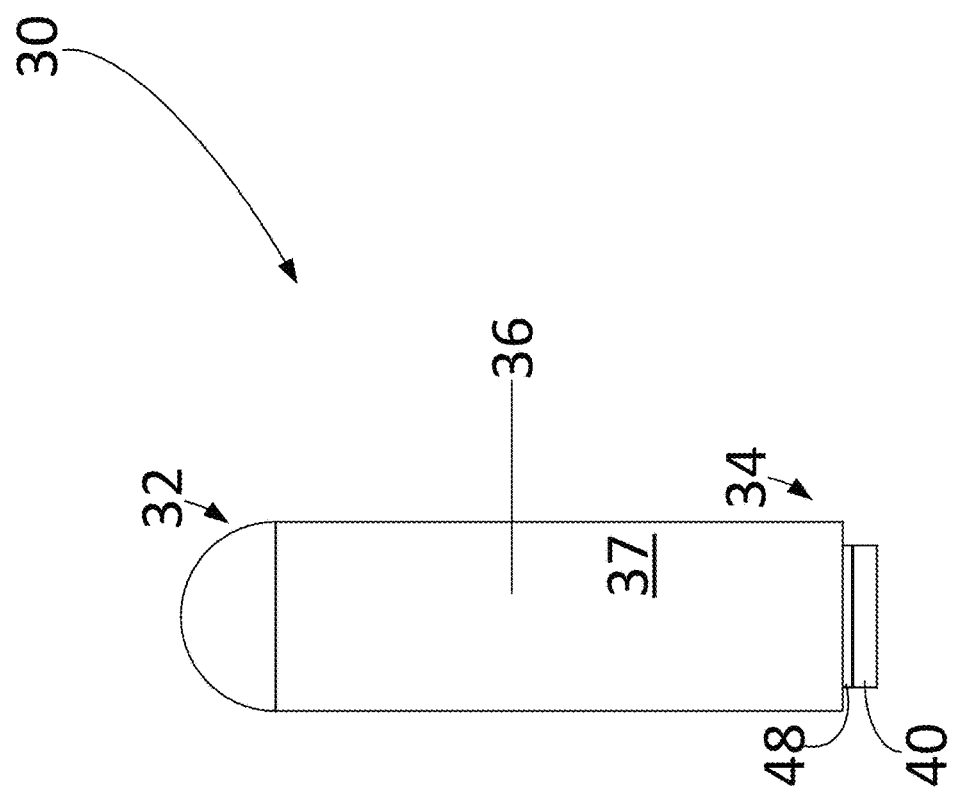

SYSTEMS AND METHODS FOR FLUID DISINFECTION WITH ULTRAVIOLET LIGHT

PRIORITY

This patent application claims priority from provisional U.S. patent application No. 62/755,041, filed Nov. 2, 2018, entitled, "SYSTEMS AND METHODS FOR FLUID DISINFECTION WITH ULTRAVIOLET LIGHT," and naming Leo J. Schowalter and Amy C. Wilson Miller as inventors, the disclosure of which is incorporated herein, in its entirety, by reference.

FIELD OF THE INVENTION

Illustrative embodiments generally relate to fluid treatment by ultraviolet light and, more particularly, the illustrative embodiments relate to a disinfection chamber having a light pipe at least partially therein.

BACKGROUND OF THE INVENTION

Fluids, including liquid water, are commonly used for many domestic and industrial purposes, such as drinking, food preparation, manufacturing, processing of chemicals, and cleansing. It often is necessary to purify a liquid prior to its use. Filters such as ceramic filters are typically used to remove particulate and chemical impurities from liquids. In addition, a liquid can be exposed to UV radiation to neutralize microorganisms and deleterious pathogens that may be present in the liquid, e.g., bacteria, viruses, and protozoa. Exposure to certain wavelengths of light can disrupt the DNA of many cellular microorganisms—virtually destroying them or rendering them substantially harmless. The exposure to UV radiation can also substantially prohibit the growth and/or reproduction of microorganisms in the liquid.

A system that uses UV radiation to irradiate fluids is often known in the art as a "UV reactor." Undesirably, conventional UV reactors often suffer from various disadvantages. Specifically, UV light is difficult to extract efficiently from UV light sources, such as light-emitting diodes (LEDs). Consequently, conventional UV reactors often only successfully utilize a fraction of the UV output of such light sources for disinfection (i.e., only a small fraction of emitted UV light is successfully introduced into the liquid to be treated). In addition, UV LEDs often generate a significant amount of heat, particularly since they must frequently be operated at higher currents (generating larger output fluxes) to compensate for inefficient light extraction.

SUMMARY OF VARIOUS EMBODIMENTS

In accordance with one embodiment of the invention, a fluid treatment system includes a reactor chamber fluidly coupled with a fluid inlet and a fluid outlet. The reactor chamber is defined by one or more chamber walls. The system includes an ultraviolent (UV) light-emitting diode. The system also includes a light pipe that extends into the reactor chamber through at least one of the chamber walls. The light pipe has a proximal end disposed outside of the reactor chamber. The proximal end is coupled with the UV LED to transmit UV light into the reactor chamber through the light pipe. To that end, the light pipe also has a distal end, opposite the proximal end, disposed within an interior volume of the reactor chamber. The light pipe includes a central section disposed between the proximal end and the distal end. The central section is configured to transmit the UV light from the one or more of the UV LEDs to the distal end.

In some embodiments, the central section of the light pipe is hollow and has a central section wall with an inner surface. The inner surface of the central section wall may have, or may be formed from, a UV reflective material. In some other embodiments, the central section of the light pipe may be solid. The central section may include an inner portion formed from a UV transmissive material, and an outer portion formed from a UV reflective material. In some embodiments, at least a portion of the central section of the light pipe is coated with a UV reflective material. The UV reflective material may be aluminum, and/or a fluoropolymer such as PTFE.

The UV light is transmitted into the reactor chamber through the distal end. To that end, at least a portion of the distal end may be roughened or textured. In some embodiments, the central section of the at least one light pipe may also be roughened or textured. The distal end of the light pipe extends into the reactor chamber through a chamber wall. At least a portion of the chamber wall through which the light pipe extends may be removable from, and/or attachable to, the reactor chamber.

The LED may be coupled to the light pipe by an attachment material. In preferred embodiments, the attachment material is UV transmissive. Among other things, the light pipe may be formed from quartz, fused silica, and/or sapphire. The chamber walls may be formed from material reflective to UV light. In some embodiments, the UV reflective material is aluminum, and/or a fluoropolymer. The UV LED may be configured to emit UV light having a wavelength ranging between approximately 200 nm and approximately 320 nm. More specifically, the UV LED may be configured to emit UV light having a wavelength ranging between approximately 250 nm and approximately 275 nm.

In accordance with another embodiment, a UV reactor has one or more walls that define a disinfection chamber. The disinfection chamber is configured to have fluid flowing therethrough. The UV reactor also has a UV LED configured to transmit UV light into the disinfection chamber through a light pipe. The light pipe has a proximal end, a distal end, and a central section disposed between the proximal end and the distal end. The distal end extends into the disinfection chamber through a wall of the disinfection chamber. The proximal end is outside of the disinfection chamber and is coupled with the UV LED. The central section has a UV-reflective portion configured to reflect UV light.

In some embodiments, the central section of the light pipe is entirely disposed within a chamber wall. A diameter of the distal end of the light pipe may be larger than a diameter of the central section. A seal may be formed between the light pipe and an interior volume of the disinfection chamber. Among other things, the seal may include an O-ring.

In accordance with yet another embodiment, a method disinfects fluid by providing a fluid treatment system. The fluid treatment system has a reactor chamber fluidly coupled to a fluid inlet and a fluid outlet. The reactor chamber is enclosed by one or more chamber walls. The system includes a UV LED. The system also includes a light pipe that extends into the reactor chamber through at least one of the chamber walls. The light pipe has a proximal end disposed outside of the reactor chamber. The UV LED is coupled to the proximal end to transmit UV light into the reactor chamber through the light pipe. The light pipe also has a distal end, opposite the proximal end, that is disposed within an interior volume of the reactor chamber. The light pipe also has a central section disposed between the proximal end and the distal end. The central section is configured to transmit the UV light from the UV LED to the distal end. The method flows fluid through the fluid inlet into the reactor chamber. The method also activates the UV LED.

Illustrative embodiments may electrically couple the UV LED to a power source using one or more conductive contacts. In some embodiments the one or more of the conductive contacts may be configured to urge at least one UV LED toward the proximal end of the light pipe. Among other things, the one or more of the conductive contacts may be a spring contact.

The disinfection chamber may include a main section and a submodule that are removably couplable. The light pipe may extend through a chamber wall of the submodule. The method may thread the submodule with the main section. To that end, a portion of the submodule may be threaded, and a portion of the main section may be complementarily threaded.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 1B schematically shows the light pipe of the UV reactor on FIG. 1A.

DESCRIPTION OF ILLUSTRATIVE EMBODIMENTS

In illustrative embodiments, a light pipe 30 directly communicates ultraviolet (UV) light from a light-emitting diode (LED) 40 into a chamber 12 of a UV reactor 10. Because the light from the LED 40 is transmitted into the chamber 12 via the light pipe 30, some or all the surfaces (including a light pipe wall 22 through which the light pipe 30 extends) of the reactor 10 may be UV reflective (e.g., formed from reflective materials and/or coated with reflective material). This is in contrast to prior art methods that have a UV transmissive window coupled between the LED 40 (or other UV light source) and the chamber 12. As another benefit, the light pipe 30 acts as a heat sink that draws heat away from the LED 40. Specifically, the light pipe 30 is cooled by the fluid in the chamber 12. The cooling effect of the heat sink may allow the LED 40 to operate at or above its maximum rated power. Details of illustrative embodiments are discussed below.

Figure 1A:
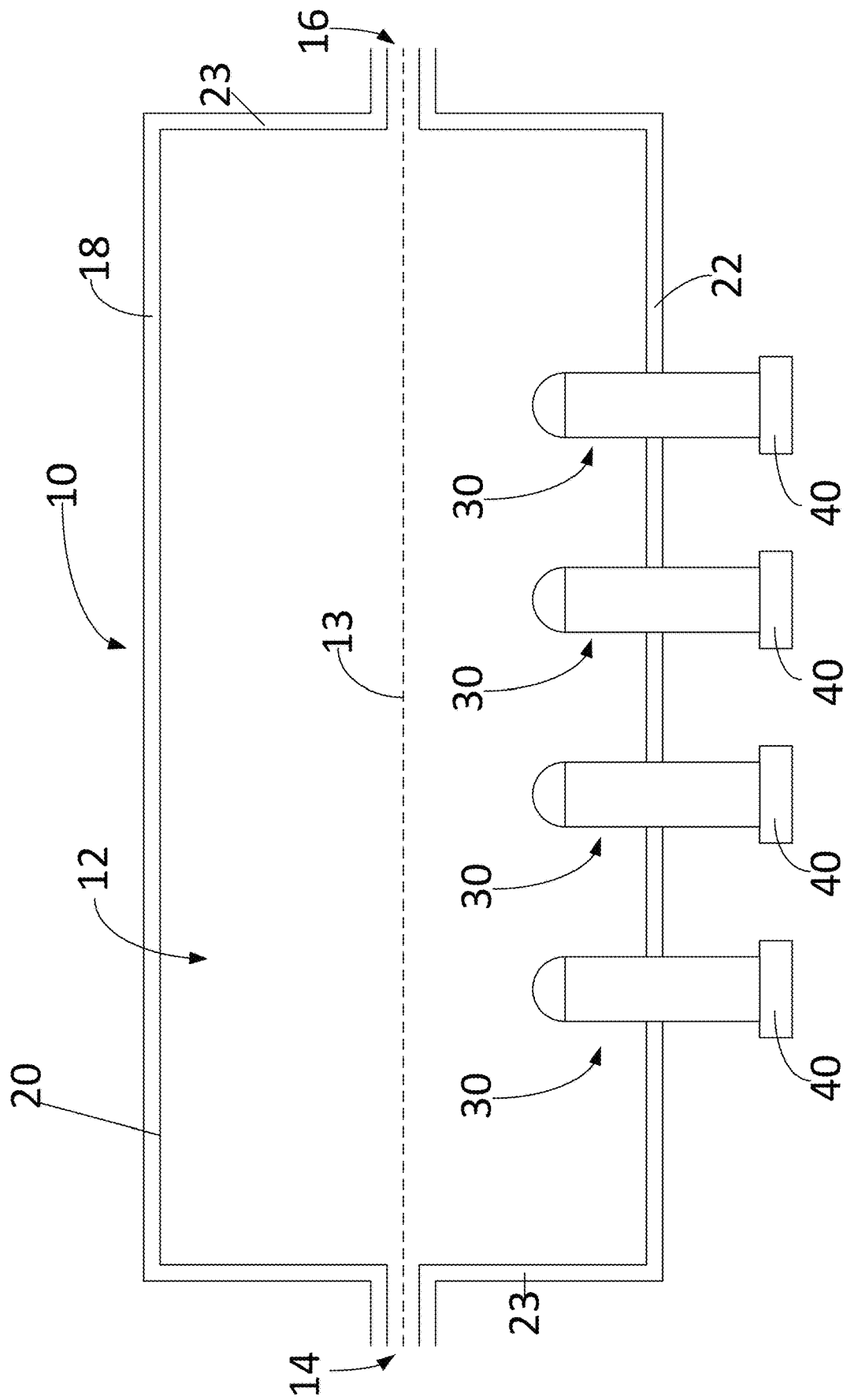
FIG. 1A schematically shows a UV reactor for disinfecting fluid in accordance with illustrative embodiments of the invention.

FIG. 1A schematically shows a UV reactor 10 for disinfecting fluid in accordance with illustrative embodiments of the invention. The UV reactor 10 has an inlet 14 through which fluid enters a chamber 12 (also referred to as a flow cell 12 of the reactor 10). The inlet 14 may be coupled to a fluid source (e.g., water line that provides drinking water). At the other end of the UV reactor 10 is an outlet 16 through which fluid exits the chamber 12 (e.g., towards a faucet). While illustrative embodiments depict the outlet 16 and inlet 14 as being on opposed sides of the chamber 12, it should be understood that the inlet 14 and the outlet 16 may be oriented anywhere on the UV reactor 10. For example, the inlet 14 and/or the outlet 16 may be positioned on the sidewall 22 of the reactor 10.

As the fluid flows through (e.g., from the inlet 14 to the outlet 16), or is stagnant in, the chamber 12, UV-emitting LEDs 40 disinfect the fluid. To that end, one or more of the above noted LEDs 40 are each coupled to a respective light pipe 30 that efficiently transfers the UV radiation into the chamber 12. The LEDs 40 may be arranged outside of the chamber 12 and along the exterior of the sidewall 22 (e.g., spaced along a longitudinal axis 13 of the reactor 10). Additionally, or alternatively, the LEDs 40 may be positioned on an end surface 23. In some embodiments, the LEDs 40 may constantly be powered on. In some other embodiments, the LEDs 40 may be triggered by fluid flow through the chamber 12. Additionally, or alternatively, the LEDs 40 may be periodically powered on or activated. Illustrative embodiments may use a variety of LED 40 dosing protocols, such as those described in U.S. Patent Application No. 62/891,503, which is incorporated herein by reference in its entirety.

FIG. 1B schematically shows a close-up view of one of the light pipes 30 coupled with one of the LEDs 40 in accordance with illustrative embodiments of the invention. The light pipe 30 has a distal end 32 and, opposite the distal end 32, a proximal end 34 coupled (e.g., using attachment material 48, such as a UV resistant adhesive) to or more UV LEDs 40. In illustrative embodiments, at least a portion of the distal end 32 of the light pipe 30 extends into the reactor chamber 12 of a UV reactor 10 (shown in FIG. 1), such that light from the UV LED 40 exits the distal end 32 and treats the fluid within the chamber 12. While illustrative embodiments describe that the LED 40 is coupled to the proximal end 34 of the light pipe 30, it should be understood that in some embodiments, the LED 40 may be formed integrally with the light pipe 30 and/or inside the light pipe 30.

The light pipe 30 also has the central section 36 disposed between the proximal end 34 and the distal end 32. The central section 36 is configured to transmit the UV light emitted from the UV LED 40 to the distal end 32 of the light pipe 30. Accordingly, the central section 36 may have UV reflective material configured to prevent and/or reduce the amount of the UV light escaping and/or being absorbed prior to entering the chamber 12. For example, the central section 36 of the light pipe 30 may be hollow and have a central section wall 37 with an inner surface (not visible). The inner surface of the central section 36 wall may be coated with a UV reflective material. Additionally, or alternatively, the central section 36 wall may be formed from UV reflective material. In some other embodiments, the central section 36 may be solid rather than hollow. For example, the central section 36 may have an inner portioned formed from a UV transmissive material, and an outer portion formed from a UV reflective material. Advantageously, in illustrative embodiments the central section 36 prevents or mitigates the loss of UV light delivered into the chamber 12 as a result of absorption and/or united transmission outside the chamber 12.

In illustrative embodiments, the light pipe 30 is formed from a material with a refractive index that is relatively high. For example, in some embodiments, the refractive index of the light pipe, or at least a portion thereof (e.g., the portion adjacent the LED 40 through which the UV-light enters the light pipe 30), has a refractive index of between about air (n=1) and about AlN (n=2.3 to 2.6 in the wavelength range of 300 nm to 220 nm). In illustrative embodiments, the high index of refraction makes it easier to couple radiation from the LED 40 into the light pipe 30 without losses due to reflection at the interface between the LED 40 and the light pipe 30.

As noted above, the light pipe 30 and the LED 40 may be coupled using the attachment material 48 (e.g., an adhesive). In various embodiments, the attachment material 48 has an index of refraction between those of the light pipe 30 and the UV LED 40. Preferably, the attachment material 48 is UV transmissive and UV stable. Advantageously, the attachment of the UV LED 40 to the light pipe 30 efficiently couples the UV light from the UV LED 40 into the light pipe 30. The light is subsequently efficiently transmitted from the light pipe 30 (e.g., via one or more textured or roughened surfaces), thereby minimizing the opportunity for the light to reflect back to the UV LED 40 where it might be absorbed. Thus, illustrative embodiments efficiently treat fluid while minimizing loss of UV light via absorption. Although illustrative embodiments refer to textured or roughened surfaces of the light pipe 30, it should be understood that some embodiments may have some or all of the surfaces described herein not textured and/or not roughened.

In some embodiments, the attachment material 48 may be silicone-based, and may include, for example, Deep UV-200 available from Schott North America, Inc. of Elmsford, N.Y. In other embodiments, the attachment material 48 may include a fluorinated polymer such as polytetrafluoroethylene (PTFE), e.g., Optical PTFE (available from Berghof Fluoroplastic Technology GmbH of Eningen, Germany), Teflon AF (available from DuPont®), or Cytop® (a polymerized perfluoro(4-vinyloxy-1-butene), available from Asahi Glass Company). In various embodiments, the attachment material 48 may include a silica-based polymer.

The distal end 32 of the light pipe 30 may be shaped to direct the light in one or more directions and/or focus the light from the UV LED 40. For example, at least a portion of the distal end 32 may be convexly curved to be substantially hemispherical, conical, frustoconical, or cylindrical. It should be understood that these shapes are merely exemplary, and that illustrative embodiments are not limited thereto.

Although the maximum of the distal end 32 is shown as being approximately the same as that of the proximal end 34 and portions 36 of the light pipe 30 therebetween, this is not intended to limit various embodiments of the invention. For example, the diameter of the distal end 32 diameter (or other lateral dimension, such as width) may be larger than that of the proximal end 34 and/or one or more portions of light pipe 30 disposed between the distal end 32 and the proximal end 34. As shown, various portions of the light pipe 30 may be substantially cylindrical and straight. However, one of skill in the art understands that the light pipe 30 may have other shapes (e.g., a substantially rectangular cross section) and/or curvature.

At least a portion of the light pipe 30 may be roughened or otherwise textured to enhance out-coupling of light from the UV LED 40 from the light pipe 30. Preferably, the distal end 32 may be roughened or textured. In various embodiments, the roughening may be in a predetermined pattern such that a larger fraction of the light is emitted from such portions of the light pipe 30. In various embodiments, only one or more portions (or even all) of the surface of the distal end 32 is roughened, such that the light is substantially only out-coupled from the distal end 32. In other embodiments, one or more other portions of the light pipe 30 are roughened such that at least a fraction of the light is emitted (e.g., laterally) from the light pipe 30. For example, the light pipe 30 may be roughened along at least a portion of the light pipe 30, where the roughness (and thus amount of out-coupled light) increases along the length of the light pipe 30 toward the distal end 32. However, in some embodiments, the light pipe 30 is not roughened and/or textured. In various embodiments, one or more portions of the light pipe 30 (e.g., one or more portions not textured or roughened for light transmission) may be coated with a material reflective to UV light to facilitate confinement of the UV light within the light pipe 30. For example, one or more portions of the light pipe 30 may be coated with aluminum and/or PTFE. In various embodiments, PTFE may be utilized due to its compatibility with a wide range of fluids that may be treated within the UV reactor 10.

Unlike visible LEDs, UVC LEDs 40 are difficult to encapsulate. The light emitting portion of a visible LED is typically plastic and is not capable of withstanding UVC exposure without rapidly being damaged. To the inventors' knowledge, there are no commercial UVC LEDs available that have a light emitting portion which could be inserted into a chamber. Commercially available UVC LEDs either have a quartz window over the light emitting portion or have a bare semiconductor surface. In addition, the plastic portion of the light emitting portion of a typical LED is a poor thermal conductor. Accordingly, illustrative embodiments of the invention may form the light pipe 30 from high thermal conductivity transparent mediums (e.g., sapphire). Additionally, illustrative embodiments may minimize the thickness of the material 48 used for the attachment of the light pipe 30. Sapphire, for example, is transparent to UVC radiation, and generally does not degrade with long term exposure. Furthermore, sapphire has a thermal conductivity of approximately 35 W/m-K, which is at least 10× (more typically, 100×) higher than a molded plastic encapsulant for a standard LED.

Furthermore, typical sealing materials (e.g., between the LED and the inside of the chamber 12) degrade and fail under UVC irradiation, which may cause the disinfection reactor chamber 12 to leak. Illustrative embodiments may use soft PTFE O-rings and/or seals that are resistant to UV (e.g., UVC radiation). The irradiance that these materials may be exposed to is high (e.g., up to 10 W/cm2 which is large compared to other UVC light sources). Inorganic materials like sapphire and quartz (UVC grade which means that UVC absorbing impurities have been removed) are more stable. Some embodiments may include sealing materials formed from fluorochemicals, like PTFE, which is also stable and UVC resistant.

In illustrative embodiments, the light pipe 30 may be formed from sapphire. Additionally, or alternatively, the light pipe 30 may be formed from one or more rigid inorganic materials such as quartz, or fused silica. The light pipe 30 may also be formed from other materials, such as materials having an index of refraction greater than 1.3 and/or that are transparent and stable during exposure to high intensity short-wavelength UV radiation.

In various embodiments, the diameter (or other lateral dimension such as width) of at least the proximal end 34 (and, in various embodiments, one or more other portions of the light pipe 30) is selected to be approximately the same, or slightly larger (e.g., approximately 5% larger, approximately 10% larger, or approximately 25% larger) than the lateral dimension of the UV LED 40, in order to minimize the thermal resistance of the light pipe 30. For example, the lateral dimension of the light pipe 30 may be at least approximately 3 mm, at least approximately 4 mm, at least approximately 5 mm, or at least approximately 10 mm, and/or may be at most approximately 20 mm, approximately 15 mm, approximately 10 mm, approximately 5 mm, or approximately 4 mm.

The thermal resistance of the light pipe 30 may also be controlled (e.g., minimized) via selection of the length of the light pipe 30 (i.e., the dimension extending from the proximal end 34 to the distal end 32). For example, the length of the light pipe 30 may be at least approximately 3 mm, at least approximately 4 mm, at least approximately 5 mm, or at least approximately 10 mm, and/or may be at most approximately 20 mm, approximately 15 mm, approximately 10 mm, approximately 5 mm, or approximately 4 mm. In some embodiments, the distal end 32 may be positioned so that it does not extend internally beyond the wall 22 of the reactor 10. For example, the distal end 32 may be flush with the inner surface of the light pipe wall 22.

The reactor 10 may be embodied in a small device. The inventors recognized that the surface area of the aperture through which the light pipe 30 passes may take up a disproportionately high amount of the internal surface area of the chamber 12. For example, some prior art apertures known to the inventors may take up to 30-50 percent of the total surface area of the chamber 12. Undesirably, this significantly reduces the amount of surface area of the chamber 12 that can reflect incoming UV light, adversely affecting uniform fluid treatment.

Accordingly, as described in U.S. Patent Application No. 62/836,793, which is incorporated herein by reference in its entirety, illustrative embodiments of the invention may minimize the size of the aperture relative to the overall surface area of the interior walls of the chamber 12.

A person of skill in the art understands that illustrative embodiments of the invention may provide a number of advantages. For example, UVC LEDs 40 preferably are kept cool (e.g., ideally close to room temperature) during operation. Typically, the UVC LEDs 40 are heat sunk by extracting heat out of the back of the package 42. However, heat sinks are typically larger than the LED 40 and may add substantial cost. Illustrative embodiments advantageously extract heat from the UVC LED 40 out of the same surface as the radiation emission surface, and use the fluid being disinfected as the heat sink. Accordingly, illustrative embodiments may operate without a traditional heat sink arrangement, which extracts heat sink from the rear of the LED 40 (i.e., opposite direction of light emission). The standard heat sink arrangement requires a costly LED mounting arrangement. For instance, a printed circuit board (PCB) with metal core (i.e., for heat sinking an LED), may cost 10× what a standard (FR4) PCB costs. This metal-core PCB must then also be heat sunk; either to the ambient at additional cost or back to the fluid with additional complication and cost. Accordingly, some embodiments advantageously avoid the use of the traditional heat sink mounting configuration.

Figure 2A:
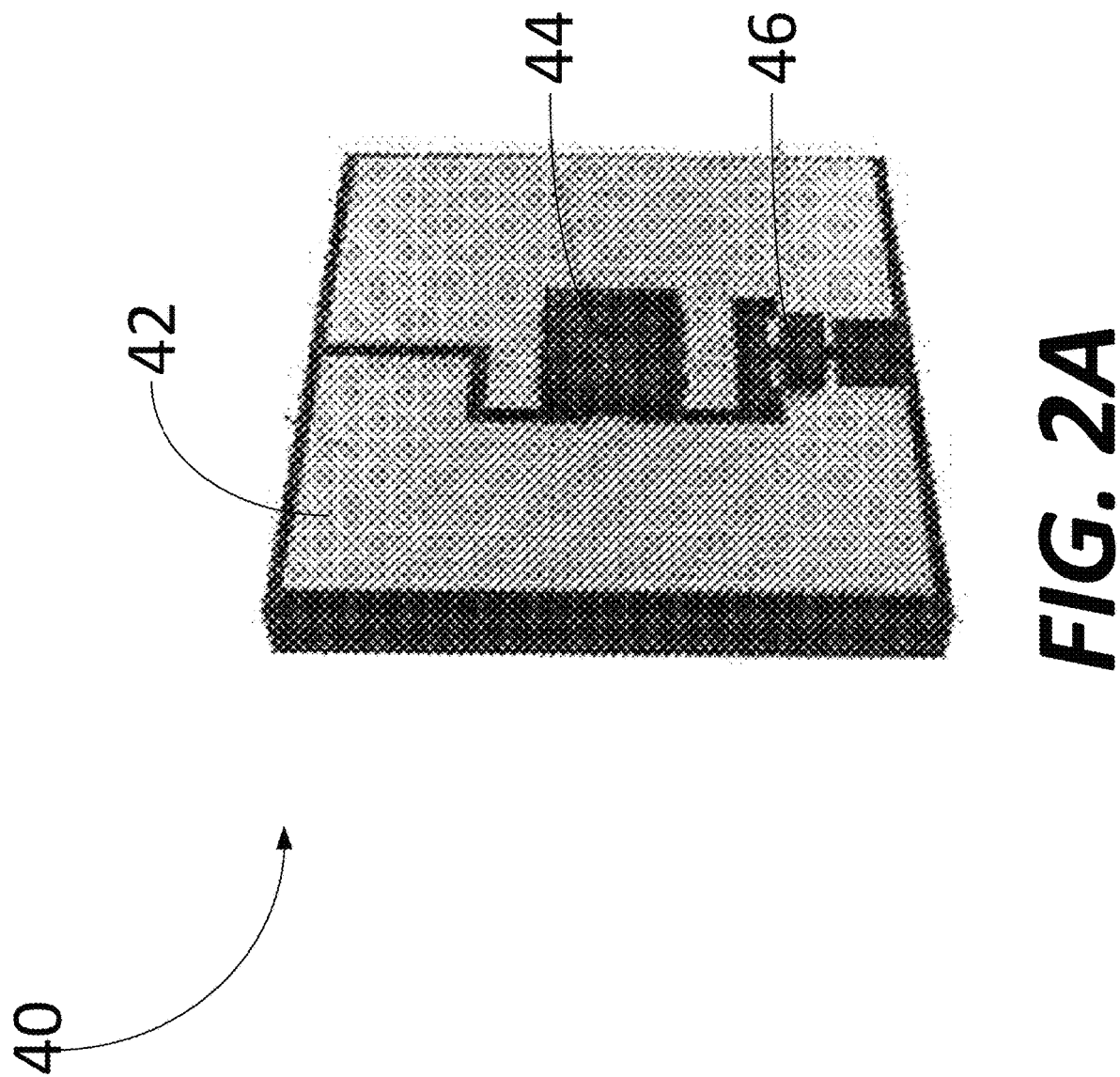
FIG. 2A schematically shows a perspective view of a UV LED in accordance with illustrative embodiments of the invention.
Figure 2B:
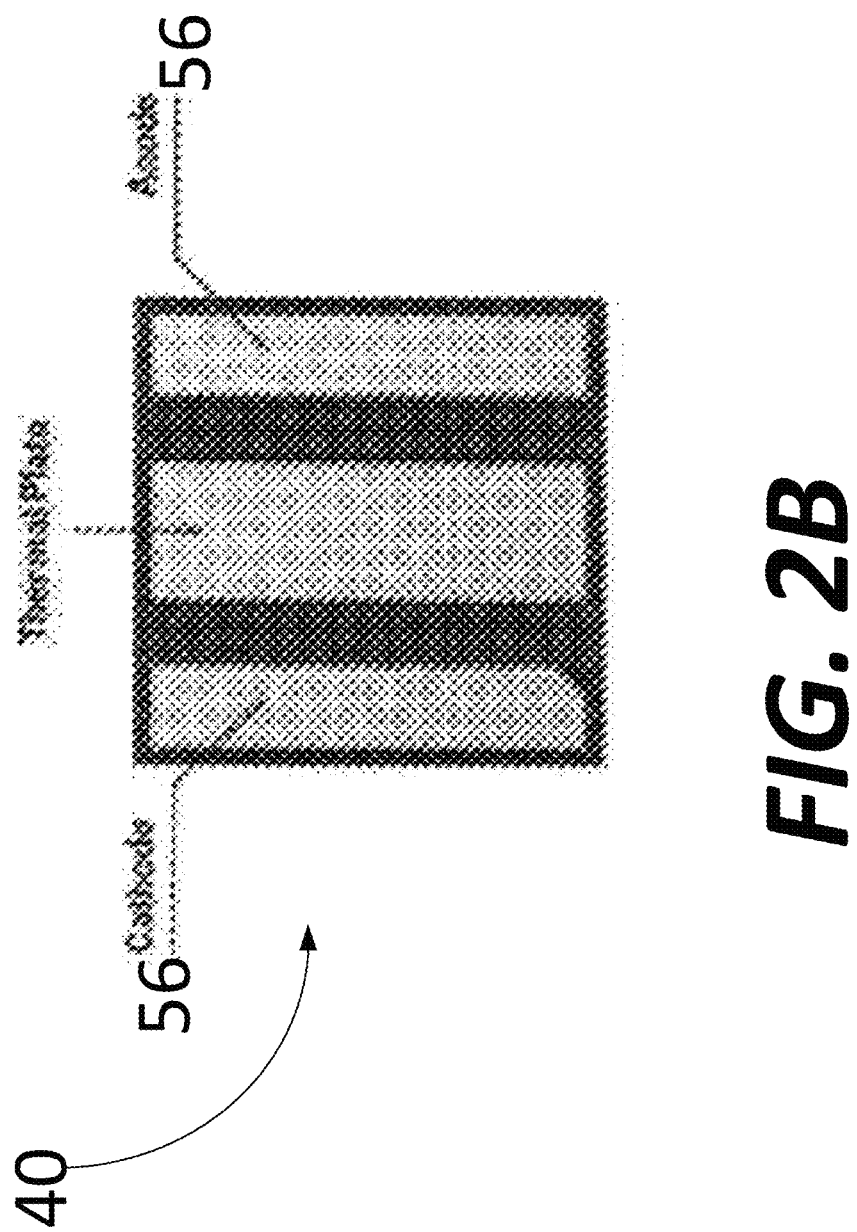
FIG. 2B schematically shows a plan view of the back surface of the UV LED shown in FIG. 2A.

FIG. 2A schematically shows a perspective view of a UV LED 40 in accordance with illustrative embodiments of the invention. FIG. 2B schematically shows a plan view of the back surface of the UV LED 40 shown in FIG. 2A. As shown, the UV LED 40 may include one or more LED chips (packaged or unpackaged) 44 mounted on a submount or substrate package 42. The LED 40 may be surface mounted (i.e., placed directly) onto the surface of a printed circuit board 54 (e.g., see FIG. 2C). In various embodiments, the UV LED 40 is configured to emit UV light, e.g., light within at least a portion of the wavelength range of approximately 100 nm to approximately 320 nm. In various embodiments, the UV LED 40 may also include one or more other electronic components 46 (e.g., a voltage regulator, such as a Zener diode). The electronic component 46 may protect the LED chip 44 from short circuits or electrostatic discharge (ESD) events. In various embodiments, the electronic component 46 may include one or more avalanche breakdown diodes and/or one or more silicon-controlled rectifiers. In various embodiments, the electronic component 46 may include a resistor and one or more diodes; for example, the resistor may be electrically connected in series with the one or more diodes.

FIG. 2A also schematically shows the UV LED 40 on the substrate package 42. The package 42 may include one or more plastics (e.g., part of a lead frame package), such as polyphthalamide (PPA) and/or one or more ceramics, such as aluminum nitride and/or alumina. In various embodiments, one or more portions of a surface of the package 42 may be coated with a material reflective to UV light (e.g., aluminum or PTFE) and/or that is electrically and/or thermally conductive (e.g., one or more metals).

As shown in FIG. 2B, the back side of the UV LED 40 may have thereon one or more contacts for electrical coupling to the UV LED 40. For example, as shown in FIG. 2B, the back side of UV LED 40 may have an anode contact 56 and a cathode contact 56. Such contacts 56 may electrically couple to the LED chip 44 through the thickness of the package 42, e.g., through one or more vias or other connectors disposed within the package 42. As also shown in FIG. 2B, the back side of the UV LED 40 may have a thermal plate for further dissipation of heat generated by the UV LED 40. The thermal plate may therefore include one or more thermally conductive materials (e.g., one or more metals, e.g., copper, gold, aluminum, etc.).

In illustrative embodiments, the UV LED 40 is formed with an aluminum nitride (AlN) substrate with one or more quantum wells and/or strained layers, including AN, gallium nitride (GaN), indium nitride (InN), or binary or tertiary alloy thereof. The UVC LED 40 preferably has a substrate and/or device structure resembling those detailed in U.S. Pat. No. 7,638,346, filed on Aug. 14, 2006, U.S. Pat. No. 8,080,833, filed on Apr. 21, 2010, and/or U.S. Patent Application Publication No. 2014/0264263, filed on Mar. 13, 2014, the disclosures of which are incorporated herein, in their entireties, by reference. As known to those of skill in the art, the specific semiconductor materials and layer structure of the UV LED 40 may be selected so that a desired specific wavelength (or wavelength range) of light is emitted by the UV LED 40. In various embodiments of the invention, the UV LED 40 may be a well know, commercially available device, such as the KLARAN™ UV LED, distributed by Crystal IS, Inc. and Asahi Kasei.

In various embodiments, the UV LED 40 is also urged toward and/or attached to the proximal end 34 of the light pipe 30 by electrical contacts 56 that are also utilized to supply power to the UV LED 40. For example, one or more spring contacts may be utilized that each make contact to one of the back-side contacts of the UV LED 40. In various embodiments of the invention, the use of such spring contacts is facilitated because no additional thermal management (e.g., heat sinking) is needed on the back side of the UV LED 40; instead, heat is extracted from the UV LED 40 via the light pipe 30 itself (and, in various embodiments, from the light pipe 30 to the fluid being treated).

Figure 2C:
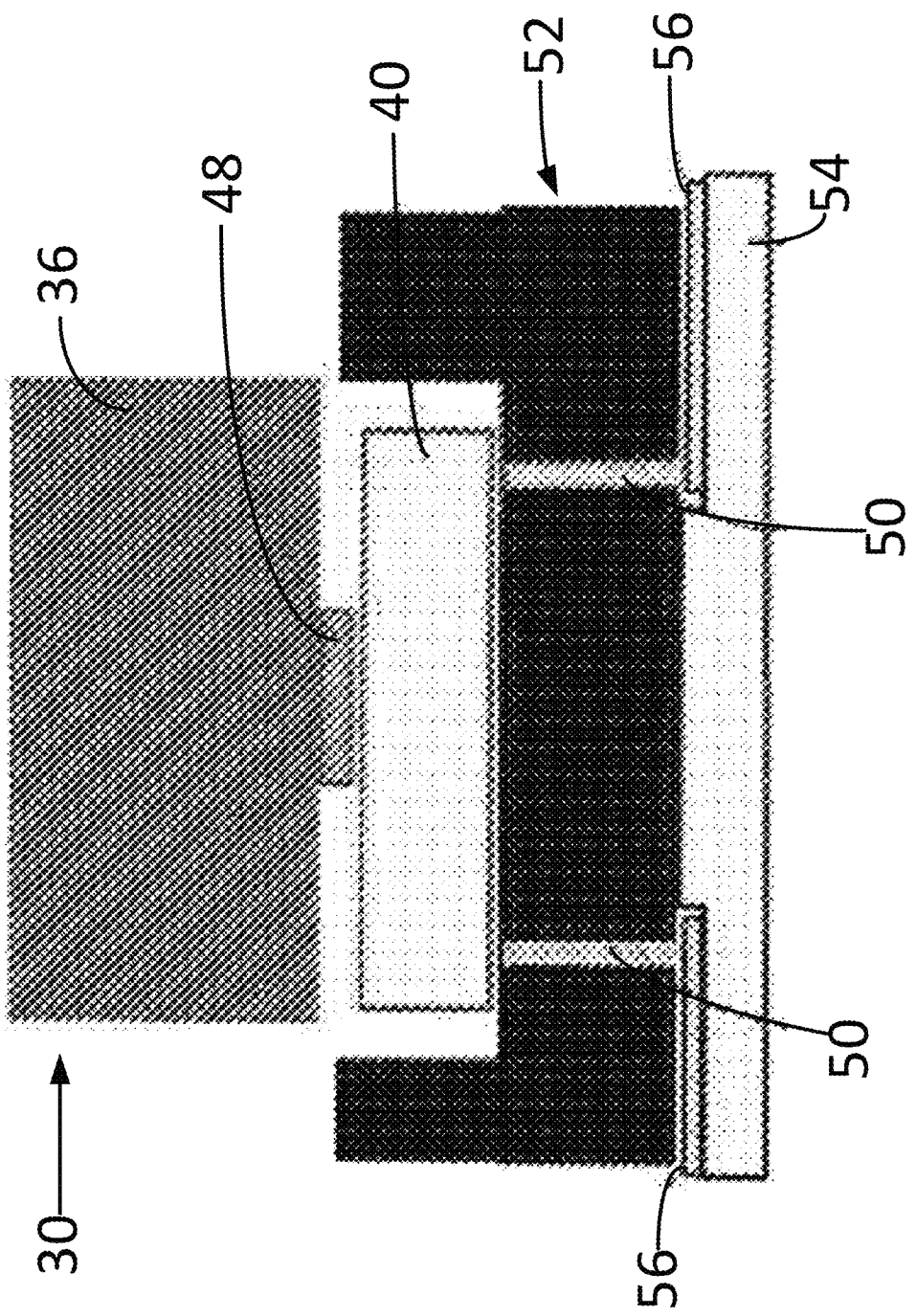
FIG. 2C schematically shows a cross-section of the UV LED attached to the light pipe in accordance with illustrative embodiments of the invention.
Figure 2D:
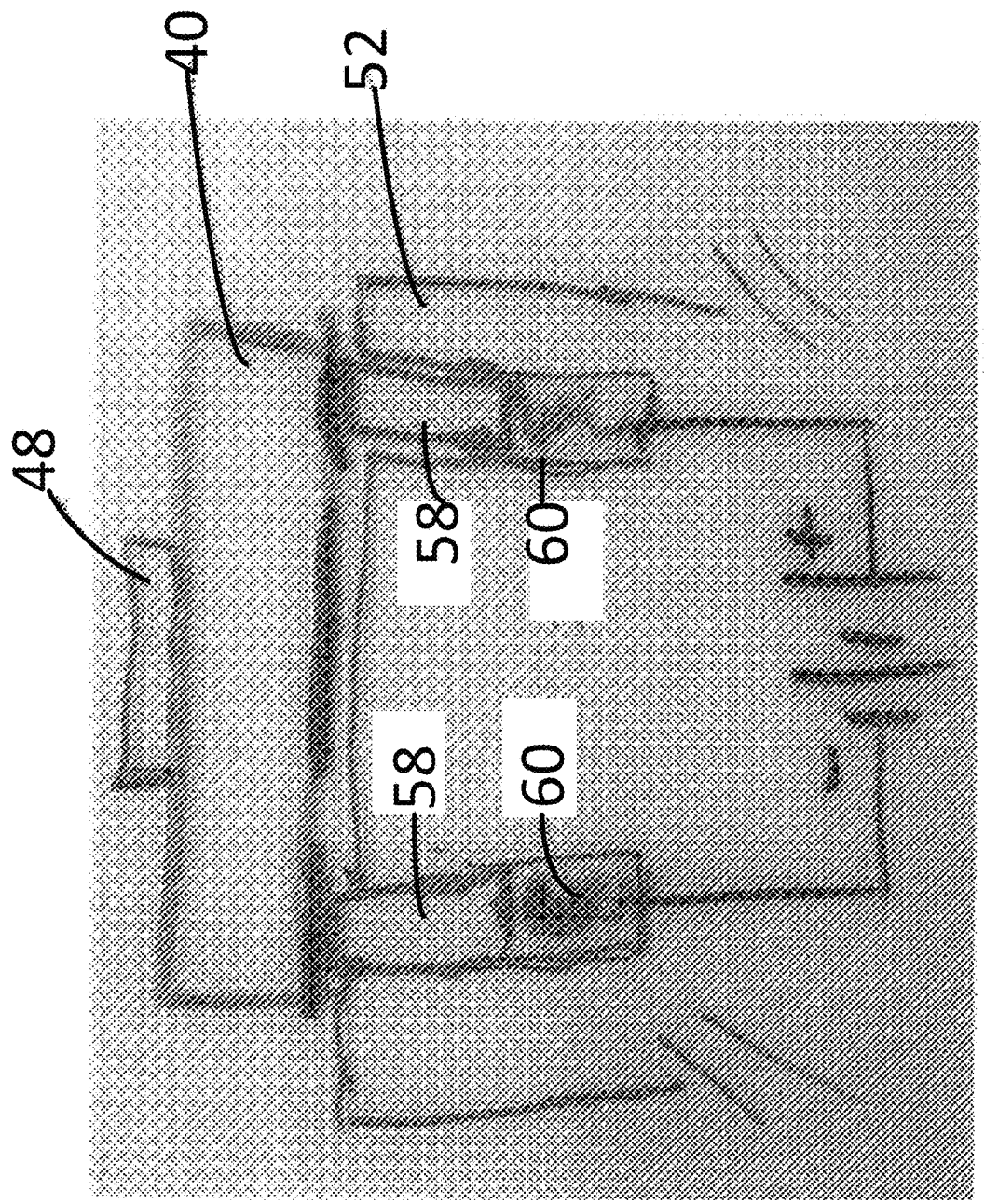
FIG. 2D schematically shows details of spring contacts in accordance with illustrative embodiments of the invention.

FIGS. 2C and 2D schematically show an electrical-connection scheme for the UV LED 40 in accordance with illustrative embodiments of the invention. FIG. 2C schematically show a cross-sectional schematic depicting the UV LED 40 attached to a central section 36 of the light pipe 30 via an attachment material 48 (note that the remainder of the light pipe 30, including the distal end 32, is not shown in FIG. 2C). As shown, power is supplied to the UV LED 40 via spring contacts 50 that extend through and are electrically isolated from a base 52. The base 52 may be formed from one or more suitably rigid materials, e.g., metals such as aluminum. In various embodiments, the base 52 may be thermally conductive. As shown, the base 52 may be electrically and/or mechanically attached to a printed circuit board 54 containing electrical contacts 56 that themselves are electrically coupled to a source of power for UV LED 40 (e.g., a power supply, not shown).

FIG. 2D schematically shows more details of the spring contacts 50 in accordance with illustrative embodiments of the invention. As shown, each spring contact 50 may include a contact pin 58 and a spring 60 that is configured to urge the contact pin 58 toward the UV LED 40 and make electrical contact thereto. In various embodiments, electrical and mechanical contact between the contact pins 58 and the electrical contacts of UV LED 40 is made only via the spring force imparted by the springs 60. That is, in some embodiments of the invention, no other coupling material (e.g., solder, adhesive, etc.) may be present between the contact pins 58 and the electrical contacts of UV LED 40. As utilized herein, the term "spring" includes any elastic entity, member, or object that reversibly stores mechanical energy. Exemplary springs include coil springs, wave springs, disc springs, leaf springs, Belleville springs (i.e., coned disc springs), and/or bellows.

Figure 3:
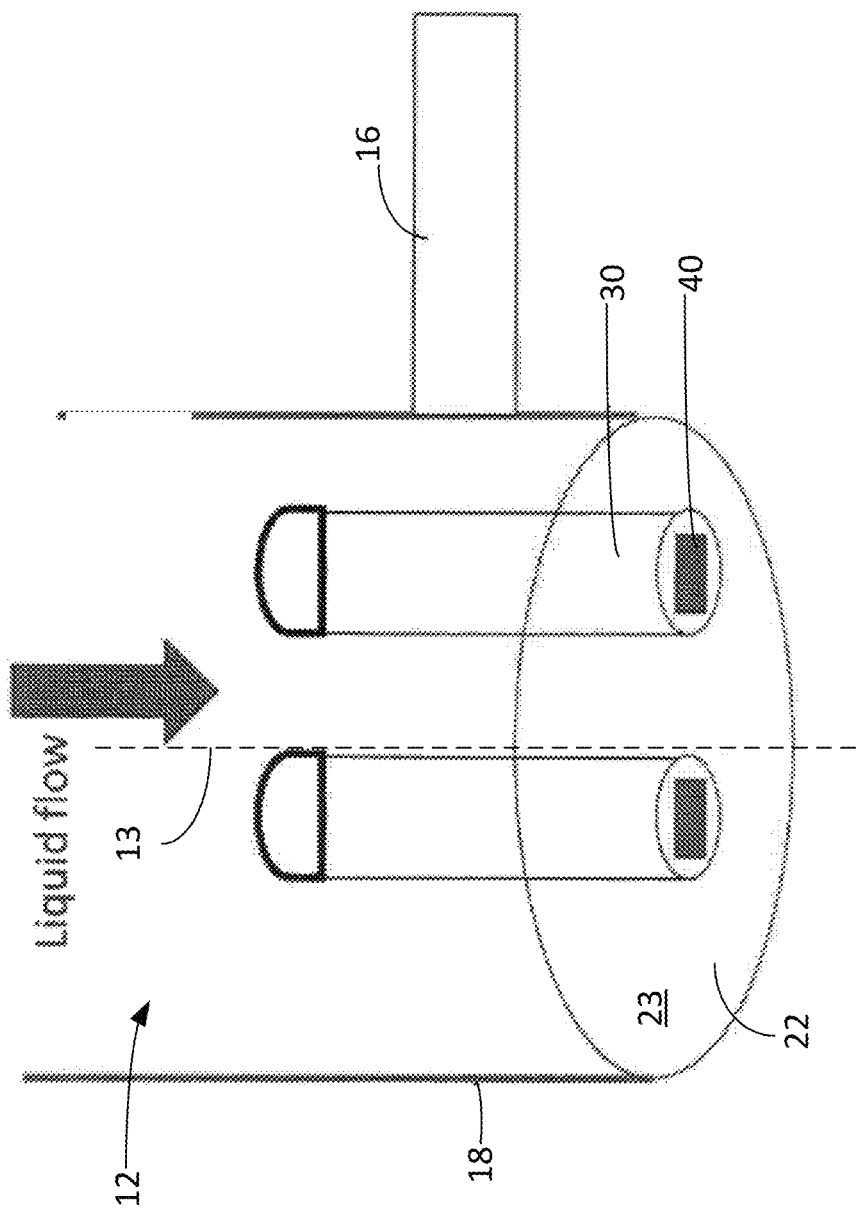
FIG. 3 schematically shows a partial schematic of a UV reactor in accordance with illustrative embodiments of the invention.

FIG. 3 schematically shows a partial schematic of a UV reactor 10 in accordance with various embodiments of the present invention. As described previously, the reactor chamber 12 has liquid flowing therethrough to be treated by UV light. As opposed to FIG. 1, in FIG. 3, the light pipes 30 are generally parallel with and spaced transverse to the longitudinal axis 13 (shown in dashed lines). Furthermore, the light pipe wall 22 includes the end surface 23 rather than the sidewall 18. The fluid flows into the reactor chamber 12 via the fluid inlet 14 and exits the reactor chamber 12 after treatment via the fluid outlet 16. The reactor chamber 12 may have at least one sidewall 18 and the light pipe wall 22 through which one or more light pipes 30 penetrate into the reactor chamber 12. In some embodiments, the sidewall 18 may also be the light pipe wall 22 (e.g., as shown in FIG. 1). Additionally, or alternatively, illustrative embodiments may include more than one light pipe wall 22 (e.g., an end surface and a sidewall 18).

The reactor chamber 12 may include one or more materials compatible with the fluid to be treated, e.g., quartz. Accordingly, the reactor chamber 12, or a portion thereof, may be substantially transparent to UV light. The sidewall 18 and/or the light pipe wall 22 may be coated (e.g., on an outside surface) with a material substantially reflective to the UV light emitted from the light pipe 30, e.g., aluminum and/or PTFE. The coating may be diffusively reflective or specularly reflective, and thereby facilitates confinement of the UV light from the light pipe 30 within the reactor chamber 12—in various embodiments, the fluid is more efficiently disinfected via multiple interactions with the UV light (e.g., caused by reflections from the sidewall 18 and/or the light pipe wall 22).

In various embodiments, the UV reactor 10 is a flow-through reactor in which the fluid flows from the fluid inlet 14 to the fluid outlet 16 during treatment by UV light. In other embodiments, the UV reactor 10 may be a batch reactor in which fluid is introduced into the reactor chamber 12, treated by UV light, and then extracted through the fluid outlet 16 after all or a portion of the illumination by UV light.

One or more light pipes 30 may be at least partially inserted into the reactor chamber 12 via apertures (also referred to as openings) defined in the light pipe wall 22. After the light pipe 30 is inserted, a liquid-tight seal is preferably formed between the light pipe 30 and the light pipe wall 22 to prevent fluid leakage. For example, an O-ring may be disposed within the opening and may engage with the outer surface of the light pipe 30 after insertion thereof. The O-ring may include PTFE. Other embodiments may use silicone or other fluid-tight sealants.

While in some embodiments each light pipe 30 may be individually positioned into an opening in the light pipe wall 22, in other embodiments, multiple light pipes 30 are coupled, at their proximal surfaces 120, to a shared substrate (e.g., the printed circuit board 54) and extending through openings in the light pipe wall 22. The shared substrate may then contact the light pipe wall 22. The light pipes 30 may be coupled to the substrate via, e.g., soldering or an adhesive (e.g., a conductive adhesive).

As mentioned above, one or more portions 32-36 of the light pipe 30 may be roughened or textured to enhance light extraction from such surfaces, thereby directing the UV light in particular directions and/or locations within the reactor chamber 12. A plurality of the light pipes 30 may be roughened such that the light from the light pipes 30 is configured to focus on a particular area and/or along a particular direction within the reactor chamber 12. For example, one or more portions of the distal end 32 of each of the light pipes 30 may be roughened such that the light from the light pipes 30 is directed toward a central axis 13 of the reactor chamber 12 and/or toward the sidewall 18. In various embodiments, the light from the light pipes 30 may be directed toward the fluid outlet 16.

Furthermore, in some embodiments the emission surface of the LED 40 may be roughened. Illustrative embodiments may match the index of the light pipe 30 to the LED 40 emission surface, such that more of the emitted radiation is captured into the light pipe 30 without being reflected. The roughening of the LED 40 emission surface may help in some situations (e.g., where there is still a large index mismatch and the roughening helps scatter radiation that was outside the acceptance cone into the acceptance cone and, thus, into the light pipe 30).

Figure 4:
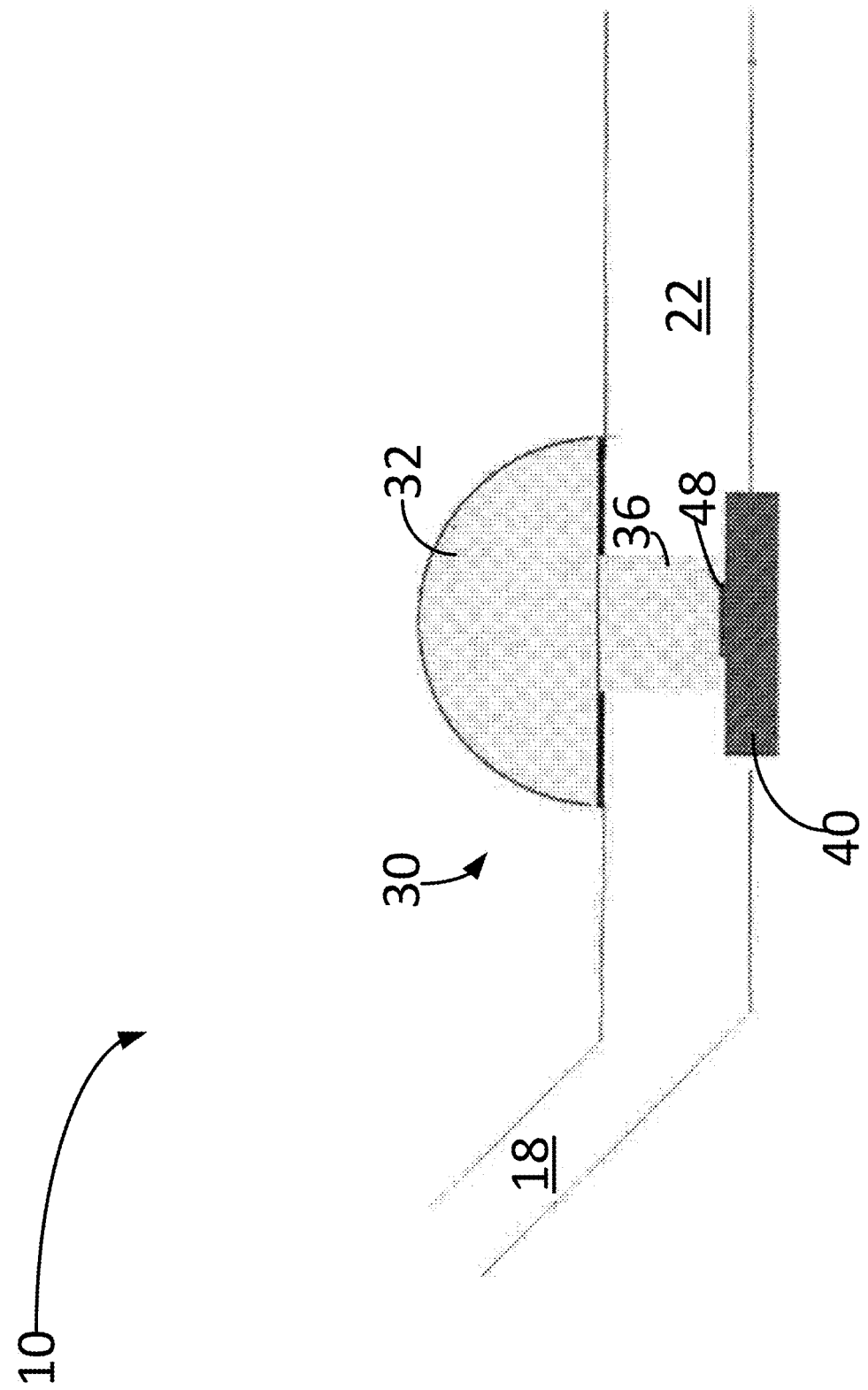
FIG. 4 schematically shows a cross-section of a portion of another embodiment of the reactor chamber in accordance with illustrative embodiments of the invention FIG. 5 schematically shows an alternative embodiment of the reactor in accordance with illustrative embodiments of the invention.

FIG. 4 schematically shows a cross-section of a portion of another embodiment of the reactor chamber 12 in accordance with illustrative embodiments of the invention. As shown, the light pipe 30 has a distal end 32 disposed within the reactor chamber 12 and that may be shaped as, for example, a hemisphere, a partial sphere, or a lens. The diameter or other lateral dimension of the distal end 32 may be larger than the central section 36 of the light pipe 30. The central section 36 may be partially or completely disposed within the light pipe wall 22. Thus, in some embodiments, the length of the central section 36 is less than or approximately equal to the thickness of the light pipe wall 22 (or the sidewall 18).

The small length of the central section 36 may advantageously minimize the thermal path of heat conducted away from the UV LED 40 via the light pipe 30. The light pipe 30 may be sealed within the light pipe wall 22 via, e.g., one or more O-rings that provide a fluid-tight seal. In various embodiments, as shown in FIG. 4, the light pipe wall 22 may be shaped or milled to enable the UV LED to be at least partially disposed within the light pipe wall 22. Such configurations may also enable the advantageous minimization of the length of the central section 36. As discussed above, the sidewall 18, end wall 23, and/or the light pipe wall 22 may include (e.g., be coated with), and/or be formed from, one or more materials diffusively or specularly reflective to UV light.

In various embodiments, the central section 36 is a portion of or window defined within the material of the light pipe wall 22. For example, the central section 36 may be defined by an opening in a reflective coating disposed over portions of the end surface. In such embodiments, the UV LED 40 may be attached directly to the window in the central section 36. The distal end 32, mounted within the reactor chamber 12, may be used to extract and focus the light from the UV LED 40.

In various embodiments, the opening in the light pipe wall 22 through which the light pipe 30 may initially be sufficiently large to accommodate insertion of the larger distal end 32 (as shown in FIG. 4). After insertion, any remaining gaps or empty space within the opening, given the smaller-diameter central section 36, may be filled with a potting material that is compatible with the fluid to be treated and, in some embodiments, reflective to UV light. For example, the potting material may include a fluoropolymer, such as PTFE.

In various embodiments, the opening in the light pipe wall 22 may include a compliant seal that is expandable to accommodate insertion of the distal end 32 and, thereafter, compresses against the central section 36 to form a fluid-tight seal. For example, the opening may have a diameter or other lateral dimension that is slightly smaller than that of the distal end 32 and/or central section 36 but that is compliant (e.g., having an inner lining including a compliant material such as expanded PTFE) and seals against the central section 36 after insertion of at least a portion of the light pipe 30.

Figure 5:
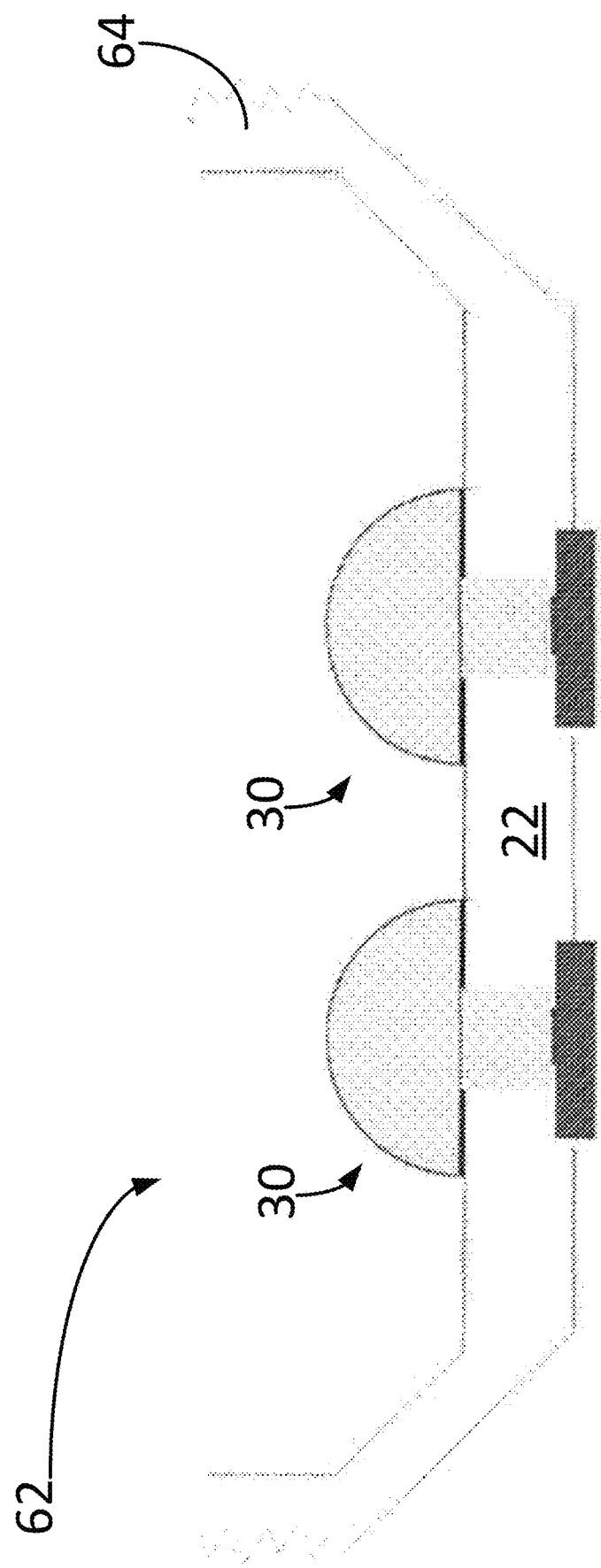

FIG. 5 schematically shows an alternative embodiment of the reactor 10. Specifically, the reactor chamber 12 is broken into a main portion coupled with a submodule 62. The submodule 62 includes one or more light pipes 30 extending through its wall. Furthermore, the submodule 62 may be modularly mateable with the remaining section of the UV reactor 10. For example, as shown in FIG. 5, the submodule 62 may include an internally UV-reflective light pipe wall 22 of the reactor chamber 12 and may feature a threaded edge 64 to replaceably mate and seal with the remaining portion of the reactor chamber 12. Such embodiments facilitate the replacement and/or servicing of components associated with the light pipes 30.

Figure 6:
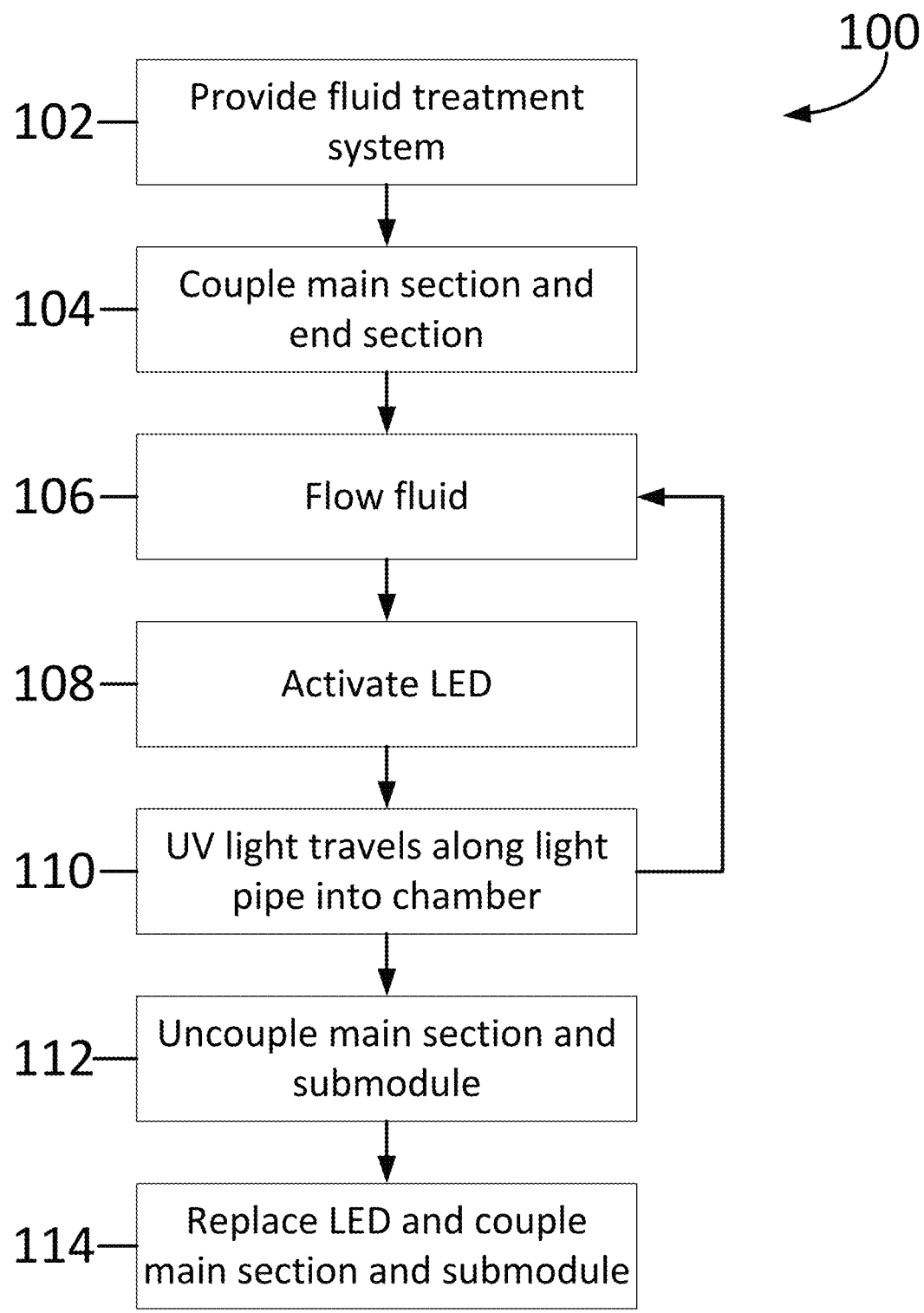
FIG. 6 shows a process of disinfecting fluid in accordance with illustrative embodiments of the invention.

FIG. 6 shows a process of disinfecting fluid in accordance with illustrative embodiments of the invention. It should be noted that this method is substantially simplified from a longer process that may normally be used. Accordingly, the method shown in FIG. 6 may have many other steps that those skilled in the art likely would use. In addition, some of the steps may be performed in a different order than that shown, or at the same time. Furthermore, some of these steps may be optional in some embodiments. Accordingly, the process 100 is merely exemplary of one process in accordance with illustrative embodiments of the invention. Those skilled in the art therefore can modify the process as appropriate. Finally, although this process is discussed with regard to activating a single UV LED 40, the process 100 of FIG. 6 can be expanded to cover using a plurality of UV LEDs 40 at the same time.

The process 100 begins at step 102, which provides the fluid treatment system. As described previously, the fluid treatment system may include the reactor chamber 12 having the inlet 14, the outlet 16, and the UV LED 40 coupled with the light pipe 30 extending through a wall of the chamber 12. In some embodiments, the reactor chamber 12 has the main section and the submodule 62, and the light pipe 30 extends through the wall of the submodule 62.

The process proceeds to step 104, which couples the main section and the submodule 62. The main section and the submodule 62 may have threads 64 that can be threadably engaged to couple the sections together. When the sections are coupled, the distal end 32 of the light pipe 30 is within the chamber 12, and the proximal end 34 and the LED 40 are outside of the chamber 12.

The process then proceeds to step 106, which flows fluid through the reaction chamber 12. The fluid may enter the chamber 12 from the inlet 14 and exit the chamber from the outlet 16. At step 108, the UV LED 40 is activated to emit UV light. Preferably, the light is UVC light having a wavelength of between about 100 nm and about 280 nm. Furthermore, the LED may be activated according to a dosing schedule described previously.

At step 110, the UV light emitted by the LTV LED 40 travels along the light pipe 30 (e.g., along the central section 36) and is transmitted into the fluid in the chamber 12 through the distal end 32. In some embodiments, the high refractive index of the material making up the light pipe 30 (e.g., sapphire) may cause the UV radiation to be totally internally reflected (i.e., unless it is approaching the surface of the light pipe 30 at close to a normal angle). Roughening the surface (e.g., at the distal end 32) may stop this total internal reflection and cause a portion of the radiation to escape even if it is outside the escape cone. The distal end 32 of the light pipe 30 may be textured or roughened to enhance UV transmission. To further facilitate transmission, the distal end 32 of the light pipe 30 may have a larger diameter than the central section 36. The process may then return to 106 and flow fluid as often as the end-user desires. As described previously, the fluid cools heat drawn from the LED 40 to the light pipe 30. Illustrative embodiments thus may use the fluid to advantageously cool the light pipe 30. At some point the fluid may stop flowing (e.g., the user no longer requests that fluid be dispensed) or fluid may continuously flow through the reactor. Either way, the process may move to the next step at any time (e.g., when the fluid stops flowing, or while fluid continues to flow).

Optionally, at step 112, the submodule 62 having the light pipe 30 may be uncoupled from the main section (e.g., when the LED 40 output power has been degraded). At step 114, the LED 40 coupled to the light pipe 30 may be replaced, and the submodule 62 may be coupled to the main section.

Disclosed embodiments, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A fluid treatment system comprising:
   a fluid inlet;
   a fluid outlet;
   a reactor chamber fluidly coupled to the fluid inlet and the fluid outlet, the reactor chamber being defined by one or more chamber walls;
   an ultraviolet (UV) light-emitting diode (LED), wherein the UV LED has a bare semiconductor surface from which UVC light is emitted;
   a light pipe extending into the reactor chamber through at least one of the chamber walls, the light pipe having:
      a proximal end disposed outside of the reactor chamber coupled to the UV LED to transmit UV light into the reactor chamber through the light pipe,
      a distal end opposite the proximal end, the distal end disposed within an interior volume of the reactor chamber, and
      a central section disposed between the proximal end and the distal end, the central section configured to transmit the UV light from the UV LED to the distal end of the light pipe; and
   a UV transmissive attachment material between the proximal end of the light pipe and the bare semiconductor surface.

2. The system of claim 1, wherein the central section of the light pipe is hollow and has a central section wall with an inner surface, the inner surface of the central section wall having, or being formed from, a UV reflective material.

3. The system of claim 1, wherein the central section of the light pipe is solid, and includes an inner portion formed from a UV transmissive material, and an outer portion formed from a UV reflective material.

4. The system of claim 1, wherein at least a portion of the distal end is roughened or textured.

5. The system of claim 1, wherein at least a portion of one of the chamber walls through which the light pipe extends is removable from and/or attachable to the reactor chamber.

6. The system of claim 1, wherein the light pipe is formed from quartz, fused silica, and/or sapphire.

7. The system of claim 1, wherein all the chamber walls include material reflective to UV light.

8. The system of claim 7, wherein the UV reflective material is aluminum, and/or a fluoropolymer.

9. The system of claim 1, wherein the UV transmissive attachment material has a material index of refraction, the light pipe having a pipe index of refraction, the UV LED having an LED index of refraction, the material index being between the pipe index and the LED index.

10. The system of claim 9, wherein the proximal end is thermally conductively coupled with the UV LED.

11. A UV reactor comprising:
    one or more walls defining a disinfection chamber, the disinfection chamber configured to have fluid flowing therethrough,
    an ultraviolet (UV) light-emitting diode (LED) configured to transmit UV light into the disinfection chamber;
    a light pipe having a proximal end, a distal end, and a central section disposed between the proximal end and the distal end,
       the distal end extending into the disinfection chamber through a wall of the disinfection chamber,
       the proximal end being outside of the disinfection chamber and being coupled with the UV LED, and
       the central section having a UV-reflective portion configured to reflect UV light; and
    a UV transmissive attachment material between the proximal end of the light pipe and a bare semiconductor surface, wherein the UV transmissive attachment material has a material index of refraction, the light pipe having a pipe index of refraction, the UV LED having an LED index of refraction, the material index being between the pipe index and the LED index.

12. The reactor of claim 11, wherein the central section of the light pipe is entirely disposed within a chamber wall.

13. The reactor of claim 11, wherein a cross-sectional dimension of the distal end of the light pipe is larger than a cross-sectional dimension of the central section.

14. The reactor of claim 11, further comprising a seal formed between the light pipe and an interior volume of the disinfection chamber.

15. The system of claim 14, wherein the seal comprises one or more O-rings.

16. The reactor of claim 11, wherein the UV LED has a bare semiconductor surface from which UVC light is emitted.

17. A method of disinfecting fluid, the method comprising:
    providing a fluid treatment system, the fluid treatment system including:
       a reactor chamber fluidly coupled to a fluid inlet and a fluid outlet, the reactor chamber enclosed by one or more chamber walls,
       one or more ultraviolet (UV) light-emitting diodes (LEDs), the one or more UV LEDs having a bare semiconductor surface from which UVC light is emitted, and
       a light pipe extending into the reactor chamber through at least one of the chamber walls, the light pipe having:
          a proximal end disposed outside of the reactor chamber,
          the UV LED coupled to the proximal end to transmit UV light into the reactor chamber through the light pipe,
          a distal end, opposite the proximal end, and disposed within an interior volume of the reactor chamber, and
          a central section disposed between the proximal end and the distal end, the central section configured to transmit the UV light from the one or more of the UV LEDs to the distal end, and
       a UV transmissive attachment material between the proximal end of the light pipe and the bare semiconductor surface, wherein the UV transmissive attachment material has a material index of refraction, the light pipe having a pipe index of refraction, the UV LED having an LED index of refraction, the material index being between the pipe index and the LED index;
    flowing the fluid through the fluid inlet into the reactor chamber; and
    activating the one or more UV LEDs.

18. The method of claim 17, further comprising electrically coupling the one or more UV LEDs to a power source using one or more conductive contacts.

19. The method of claim 18, wherein one or more of the conductive contacts is configured to urge at least one UV LED toward the proximal end of the light pipe.

20. The method of claim 18, wherein the one or more of the conductive contacts is a spring contact.

21. The method of claim 17, wherein (i) the disinfection chamber includes a main section and a submodule, (ii) the light pipe extends through a chamber wall of the submodule, and (iii) the submodule is removably coupleable with the main section.

22. The method of claim 21, further comprising threading the submodule with the main section.

* * * * *